(12) United States Patent
Marnay et al.

(10) Patent No.: US 8,795,371 B2
(45) Date of Patent: *Aug. 5, 2014

(54) INTERVERTEBRAL IMPLANT

(75) Inventors: Thierry Marnay, Montpellier (FR); Boris Beyersdorff, Berlin (DE)

(73) Assignee: DePuy Synthes Products, LLC, Raynham, MA (US)

( * ) Notice: Subject to any disclaimer, the term of this patent is extended or adjusted under 35 U.S.C. 154(b) by 941 days.

This patent is subject to a terminal disclaimer.

(21) Appl. No.: 11/766,182

(22) Filed: Jun. 21, 2007

(65) Prior Publication Data

US 2007/0265707 A1    Nov. 15, 2007

Related U.S. Application Data

(63) Continuation of application No. 10/998,951, filed on Nov. 30, 2004, now Pat. No. 8,506,634, which is a continuation of application No. 10/018,402, filed as application No. PCT/EP99/04628 on Jul. 2, 1999, now Pat. No. 6,936,071.

(51) Int. Cl.
*A61F 2/44*        (2006.01)

(52) U.S. Cl.
USPC ...................................................... 623/17.14

(58) Field of Classification Search
USPC ............ 623/14.12, 20.28–20.3, 20.32–20.33, 623/21.18, 17.11–17.16
See application file for complete search history.

(56) References Cited

U.S. PATENT DOCUMENTS

| 114,816 A | 5/1871 | Hiestand |
|---|---|---|
| 3,320,951 A | 5/1967 | Wittebol |
| 3,486,505 A | 12/1969 | Morrison |

(Continued)

FOREIGN PATENT DOCUMENTS

| CH | 624573 A5 | 8/1981 |
|---|---|---|
| DE | 2 263 842 | 7/1974 |

(Continued)

OTHER PUBLICATIONS

Hoogland, T. et al. (24th Annual ORS, Dallas, Texas, Feb. 21-23, 1978.

(Continued)

*Primary Examiner* — Thomas J Sweet
*Assistant Examiner* — Cheryl Miller
(74) *Attorney, Agent, or Firm* — Baker & Hostetler LLP

(57)    ABSTRACT

In an intervertebral implant, having an upper part that has a support face for a vertebra and a lower part that has a support face for an adjacent vertebra, on each of which parts engagement elements, which are accessible from one side of the intervertebral implant, for a manipulation instrument are disposed, in order to minimize the structural height of the intervertebral implant upon insertion into an intervertebral space, it is proposed that the upper part and lower part each have protrusions and recesses aimed at the respectively other part, which are offset laterally from one another in such a way that when the upper part has been brought close to the lower part they mesh with one another; and that the engagement elements on the upper part and on the lower part are each disposed in protrusions of these parts in such a way that the engagement elements of the upper part and lower part are located side by side and at least partly overlap in the direction of the height of the intervertebral implant.

10 Claims, 4 Drawing Sheets

(56) References Cited

U.S. PATENT DOCUMENTS

| Patent | Kind | Date | Inventor | Cross-ref |
|---|---|---|---|---|
| 3,510,883 | A | 5/1970 | Cathcart | |
| 3,579,829 | A | 5/1971 | Sampson | |
| 3,740,769 | A | 6/1973 | Haboush | |
| 3,875,595 | A | 4/1975 | Froning | |
| 3,903,549 | A | 9/1975 | Deyerle | |
| 3,992,726 | A * | 11/1976 | Freeman et al. | 623/23.4 |
| D243,286 | S | 2/1977 | Deyerle | |
| 4,021,864 | A | 5/1977 | Waugh | |
| 4,034,746 | A | 7/1977 | Williams | |
| 4,038,897 | A | 8/1977 | Murray et al. | |
| 4,038,987 | A | 8/1977 | Komiya | |
| 4,232,404 | A * | 11/1980 | Samuelson et al. | 623/21.18 |
| 4,309,777 | A | 1/1982 | Patil | |
| 4,349,921 | A | 9/1982 | Kuntz | |
| 4,467,802 | A | 8/1984 | Maslanka | |
| 4,470,158 | A | 9/1984 | Pappas et al. | |
| 4,545,374 | A | 10/1985 | Jacobson | |
| 4,550,450 | A | 11/1985 | Kinnett | |
| 4,622,959 | A | 11/1986 | Marcus | |
| 4,653,487 | A | 3/1987 | Maale | |
| 4,681,589 | A | 7/1987 | Tronzo | |
| 4,697,586 | A | 10/1987 | Gazale | |
| 4,714,469 | A | 12/1987 | Kenna | |
| 4,736,738 | A | 4/1988 | Lipovsek et al. | |
| 4,743,262 | A | 5/1988 | Tronzo | |
| 4,759,766 | A | 7/1988 | Buettner-Janz et al. | |
| 4,759,769 | A | 7/1988 | Hedman et al. | |
| 4,770,661 | A | 9/1988 | Oh | |
| 4,805,607 | A | 2/1989 | Englehardt et al. | |
| 4,863,476 | A | 9/1989 | Sheppard | |
| 4,874,389 | A | 10/1989 | Downey | |
| 4,875,474 | A | 10/1989 | Border | |
| 4,892,545 | A | 1/1990 | Day et al. | |
| 4,932,975 | A | 6/1990 | Main et al. | |
| 4,936,853 | A * | 6/1990 | Fabian et al. | 623/20.15 |
| 4,936,863 | A | 6/1990 | Hofmann | |
| 4,946,378 | A | 8/1990 | Hirayama et al. | |
| 4,997,432 | A | 3/1991 | Keller | |
| 5,002,576 | A | 3/1991 | Fuhrmann et al. | |
| 5,004,476 | A | 4/1991 | Cook | |
| 5,035,716 | A * | 7/1991 | Downey | 623/17.16 |
| 5,037,438 | A | 8/1991 | Davidson | |
| 5,062,850 | A | 11/1991 | MacMillan et al. | |
| 5,071,437 | A | 12/1991 | Steffee | |
| 5,108,442 | A | 4/1992 | Smith | |
| 5,122,130 | A | 6/1992 | Keller | |
| 5,171,280 | A | 12/1992 | Baumgartner | |
| 5,192,327 | A | 3/1993 | Brantigan | |
| 5,211,645 | A | 5/1993 | Baumgart et al. | |
| 5,228,455 | A | 7/1993 | Barcel | |
| 5,236,460 | A | 8/1993 | Barber | |
| 5,258,031 | A | 11/1993 | Salib et al. | |
| 5,271,737 | A | 12/1993 | Baldwin et al. | |
| 5,282,868 | A | 2/1994 | Bahler | |
| 5,290,312 | A | 3/1994 | Kojimoto et al. | |
| 5,306,308 | A | 4/1994 | Gross et al. | |
| 5,306,309 | A | 4/1994 | Wagner et al. | |
| 5,314,477 | A * | 5/1994 | Marnay | 623/17.15 |
| 5,326,366 | A | 7/1994 | Pascarella et al. | |
| 5,336,232 | A | 8/1994 | Green et al. | |
| 5,344,458 | A | 9/1994 | Bonutti | |
| 5,364,397 | A | 11/1994 | Hayes et al. | |
| 5,370,697 | A | 12/1994 | Baumgartner | |
| 5,383,888 | A | 1/1995 | Zvenyatsky et al. | |
| 5,395,317 | A | 3/1995 | Kambin | |
| 5,401,269 | A | 3/1995 | Buttner-Janz et al. | |
| 5,409,492 | A | 4/1995 | Jones et al. | |
| 5,423,825 | A | 6/1995 | Levine | |
| 5,425,773 | A | 6/1995 | Boyd et al. | |
| 5,431,658 | A | 7/1995 | Moskovich | |
| 5,443,514 | A | 8/1995 | Steffee | |
| 5,458,641 | A | 10/1995 | Ramirez Jimenez | |
| 5,484,437 | A | 1/1996 | Michelson | |
| 5,489,307 | A | 2/1996 | Kuslich et al. | |
| 5,501,654 | A | 3/1996 | Failla et al. | |
| 5,505,732 | A | 4/1996 | Michelson | |
| 5,507,816 | A * | 4/1996 | Bullivant | 623/17.15 |
| 5,507,821 | A * | 4/1996 | Sennwald et al. | 623/21.13 |
| 5,509,934 | A | 4/1996 | Cohen | |
| 5,534,029 | A | 7/1996 | Shima | |
| 5,534,030 | A | 7/1996 | Navarro et al. | |
| 5,545,229 | A | 8/1996 | Parsons et al. | |
| 5,554,191 | A | 9/1996 | Lahille et al. | |
| 5,556,431 | A | 9/1996 | Buttner-Janz et al. | |
| 5,562,736 | A | 10/1996 | Ray et al. | |
| 5,562,738 | A * | 10/1996 | Boyd et al. | 623/17.15 |
| 5,571,109 | A | 11/1996 | Bertagnoli | |
| 5,591,235 | A | 1/1997 | Kuslich | |
| 5,609,636 | A | 3/1997 | Kohrs et al. | |
| 5,658,347 | A | 8/1997 | Sarkisian et al. | |
| 5,674,296 | A | 10/1997 | Bryan et al. | |
| 5,676,701 | A * | 10/1997 | Yuan et al. | 623/17.15 |
| 5,683,465 | A | 11/1997 | Shinn et al. | |
| 5,702,469 | A | 12/1997 | Whipple et al. | |
| 5,702,486 | A | 12/1997 | Craig et al. | |
| 5,716,415 | A | 2/1998 | Steffee | |
| 5,720,751 | A | 2/1998 | Jackson | |
| 5,722,977 | A | 3/1998 | Wilhelmy | |
| 5,755,811 | A | 5/1998 | Tanamal et al. | |
| 5,776,199 | A | 7/1998 | Michelson | |
| 5,782,830 | A | 7/1998 | Farris | |
| 5,782,832 | A | 7/1998 | Larsen et al. | |
| 5,797,909 | A | 8/1998 | Michelson | |
| 5,800,547 | A | 9/1998 | Schafer et al. | |
| 5,824,094 | A | 10/1998 | Serhan et al. | |
| D401,335 | S | 11/1998 | Koros et al. | |
| 5,865,848 | A | 2/1999 | Baker | |
| 5,885,300 | A | 3/1999 | Tokuhashi et al. | |
| 5,888,226 | A | 3/1999 | Rogozinski | |
| 5,895,428 | A | 4/1999 | Berry | |
| 5,897,593 | A | 4/1999 | Kohrs et al. | |
| 5,899,901 | A | 5/1999 | Middleton | |
| 5,899,941 | A | 5/1999 | Nishijima et al. | |
| 5,951,564 | A | 9/1999 | Schroder et al. | |
| 6,006,174 | A | 12/1999 | Lin et al. | |
| 6,010,502 | A * | 1/2000 | Bagby | 606/247 |
| 6,017,342 | A | 1/2000 | Rinner | |
| 6,033,405 | A | 3/2000 | Winslow et al. | |
| 6,036,692 | A | 3/2000 | Burel et al. | |
| 6,039,763 | A | 3/2000 | Shelokov | |
| 6,042,582 | A | 3/2000 | Ray et al. | |
| 6,059,790 | A | 5/2000 | Sand et al. | |
| 6,063,088 | A | 5/2000 | Winslow | |
| 6,063,121 | A | 5/2000 | Xavier et al. | |
| 6,080,155 | A | 6/2000 | Michelson | |
| 6,083,225 | A | 7/2000 | Winslow et al. | |
| 6,086,595 | A | 7/2000 | Yonemura et al. | |
| 6,096,038 | A | 8/2000 | Michelson | |
| 6,096,080 | A | 8/2000 | Nicholson et al. | |
| 6,102,950 | A | 8/2000 | Vaccaro | |
| 6,102,954 | A | 8/2000 | Albrektsson et al. | |
| 6,110,179 | A | 8/2000 | Flivik et al. | |
| 6,113,602 | A | 9/2000 | Sand | |
| 6,113,637 | A | 9/2000 | Gill et al. | |
| 6,113,638 | A | 9/2000 | Williams et al. | |
| 6,126,660 | A | 10/2000 | Dietz | |
| 6,126,674 | A | 10/2000 | Janzen | |
| 6,146,421 | A | 11/2000 | Gordon et al. | |
| 6,156,040 | A | 12/2000 | Yonemura et al. | |
| 6,159,215 | A | 12/2000 | Urbahns et al. | |
| 6,171,339 | B1 | 1/2001 | Houfburg et al. | |
| 6,174,311 | B1 | 1/2001 | Branch et al. | |
| 6,179,874 | B1 * | 1/2001 | Cauthen | 623/17.14 |
| 6,224,599 | B1 | 5/2001 | Baynham et al. | |
| 6,238,414 | B1 | 5/2001 | Griffiths | |
| 6,241,769 | B1 | 6/2001 | Nicholson et al. | |
| 6,251,140 | B1 | 6/2001 | Marino et al. | |
| 6,261,296 | B1 | 7/2001 | Aebi et al. | |
| 6,264,655 | B1 | 7/2001 | Pisharodi | |
| 6,270,498 | B1 | 8/2001 | Michelson | |
| 6,296,647 | B1 | 10/2001 | Robioneck et al. | |
| 6,309,421 | B1 | 10/2001 | Pisharodi | |
| 6,368,350 | B1 * | 4/2002 | Erickson et al. | 623/17.14 |
| 6,368,351 | B1 | 4/2002 | Glenn et al. | |

(56) References Cited

U.S. PATENT DOCUMENTS

| | | |
|---|---|---|
| 6,368,353 B1 | 4/2002 | Arcand |
| 6,375,681 B1 | 4/2002 | Truscott |
| 6,395,030 B1 | 5/2002 | Songer et al. |
| 6,402,785 B1 | 6/2002 | Zdeblick et al. |
| 6,413,278 B1 | 7/2002 | Marchosky |
| 6,436,139 B1 | 8/2002 | Shapiro et al. |
| 6,440,142 B1 | 8/2002 | Ralph et al. |
| 6,440,168 B1 | 8/2002 | Cauthen |
| 6,440,169 B1 | 8/2002 | Elberg et al. |
| 6,447,547 B1 | 9/2002 | Michelson |
| 6,478,800 B1 | 11/2002 | Fraser et al. |
| 6,478,801 B1 | 11/2002 | Ralph et al. |
| 6,478,823 B1 | 11/2002 | Michelson |
| 6,500,206 B1 | 12/2002 | Bryan |
| 6,517,544 B1 | 2/2003 | Michelson |
| 6,558,424 B2 | 5/2003 | Thalgott |
| 6,565,574 B2 | 5/2003 | Michelson |
| 6,595,995 B2 | 7/2003 | Zdelblick et al. |
| 6,599,294 B2 | 7/2003 | Fuss et al. |
| 6,610,065 B1 | 8/2003 | Branch et al. |
| 6,613,091 B1 | 9/2003 | Zdelblick et al. |
| 6,635,060 B2 | 10/2003 | Hanson et al. |
| 6,641,582 B1 | 11/2003 | Hanson et al. |
| 6,641,614 B1 | 11/2003 | Wagner et al. |
| 6,652,533 B2 | 11/2003 | O'Neil |
| 6,652,534 B2 | 11/2003 | Zucherman et al. |
| 6,712,819 B2 | 3/2004 | Zucherman et al. |
| 6,712,825 B2 | 3/2004 | Aebi et al. |
| 6,733,505 B2 | 5/2004 | Li |
| 6,740,118 B2 | 5/2004 | Eisermann |
| 6,746,454 B2 | 6/2004 | Winterbottom et al. |
| 6,755,841 B2 | 6/2004 | Fraser et al. |
| 6,770,074 B2 | 8/2004 | Michelson |
| 6,824,565 B2 | 11/2004 | Muhanna et al. |
| 6,835,207 B2 * | 12/2004 | Zacouto et al. ............ 623/17.12 |
| 6,875,213 B2 | 4/2005 | Michelson |
| 6,896,676 B2 | 5/2005 | Zubok et al. |
| 6,936,071 B1 * | 8/2005 | Marnay et al. ............ 623/17.15 |
| 6,964,687 B1 | 11/2005 | Bernerd et al. |
| 6,966,912 B2 | 11/2005 | Michelson |
| 7,081,120 B2 | 7/2006 | Li et al. |
| 7,118,580 B1 | 10/2006 | Beyersdorff et al. |
| 7,169,182 B2 | 1/2007 | Errico et al. |
| 7,204,852 B2 | 4/2007 | Marnay et al. |
| 7,238,203 B2 | 7/2007 | Bagga et al. |
| 7,252,673 B2 | 8/2007 | Lim |
| 7,491,204 B2 | 2/2009 | Marnay |
| 7,547,309 B2 | 6/2009 | Bertagnoli et al. |
| 7,575,576 B2 | 8/2009 | Zubok et al. |
| 7,641,692 B2 | 1/2010 | Bryan et al. |
| 2002/0016633 A1 | 2/2002 | Lin et al. |
| 2002/0049497 A1 | 4/2002 | Mason |
| 2002/0072752 A1 | 6/2002 | Zucherman et al. |
| 2002/0077702 A1 | 6/2002 | Castro |
| 2002/0165612 A1 | 11/2002 | Gerber et al. |
| 2003/0083747 A1 | 5/2003 | Winterbottom et al. |
| 2003/0135275 A1 | 7/2003 | Garcia et al. |
| 2003/0208273 A1* | 11/2003 | Eisermann et al. ........ 623/17.14 |
| 2004/0030387 A1 | 2/2004 | Landry et al. |
| 2004/0143332 A1 | 7/2004 | Krueger et al. |
| 2004/0215198 A1 | 10/2004 | Marnay et al. |
| 2004/0225295 A1 | 11/2004 | Zubok et al. |
| 2005/0021042 A1 | 1/2005 | Marnay et al. |
| 2005/0143747 A1 | 6/2005 | Zubok et al. |
| 2005/0143749 A1 | 6/2005 | Zalenski et al. |
| 2005/0165408 A1 | 7/2005 | Puno et al. |
| 2005/0228500 A1 | 10/2005 | Kim et al. |
| 2005/0251260 A1 | 11/2005 | Gerber et al. |
| 2006/0030856 A1 | 2/2006 | Drewry et al. |
| 2006/0030860 A1 | 2/2006 | Peterman |
| 2006/0041313 A1 | 2/2006 | Allard et al. |
| 2006/0064100 A1 | 3/2006 | Bertagnoli et al. |
| 2006/0089656 A1 | 4/2006 | Allard et al. |
| 2006/0100633 A1 | 5/2006 | Michelson |
| 2006/0149273 A1 | 7/2006 | Ross et al. |
| 2006/0210594 A1 | 9/2006 | Trieu |
| 2006/0235533 A1 | 10/2006 | Blain |
| 2006/0241641 A1 | 10/2006 | Albans et al. |
| 2006/0265077 A1 | 11/2006 | Zwirkoski |
| 2007/0162134 A1 | 7/2007 | Marnay |
| 2008/0140204 A1 | 6/2008 | Heinz |
| 2009/0069894 A1 | 3/2009 | Duggal et al. |
| 2009/0076608 A1 | 3/2009 | Gordon et al. |
| 2010/0070042 A1 | 3/2010 | Bryan et al. |
| 2010/0217395 A1 | 8/2010 | Bertagnoli et al. |
| 2011/0295374 A1 | 12/2011 | Bryan et al. |

FOREIGN PATENT DOCUMENTS

| | | |
|---|---|---|
| DE | 28 04 936 | 8/1979 |
| DE | 3 023 353 | 4/1981 |
| DE | 3526742 | 1/1987 |
| DE | 4328690 | 3/1995 |
| EP | 0077159 | 4/1983 |
| EP | 0471821 | 2/1992 |
| EP | 0333990 | 7/1993 |
| EP | 0712607 | 2/2002 |
| FR | 2 718 635 | 10/1995 |
| FR | 2 724 108 | 3/1996 |
| FR | 2 737 656 | 2/1997 |
| FR | 2 742 653 | 6/1997 |
| FR | 2795945 | 1/2001 |
| JP | 2-261446 | 10/1990 |
| WO | WO 91/13598 | 9/1991 |
| WO | WO 98/34552 | 8/1998 |
| WO | WO 01/01893 | 1/2001 |
| WO | WO 01/19295 | 3/2001 |
| WO | WO 02/071986 | 9/2002 |
| WO | WO 03/053290 | 7/2003 |

OTHER PUBLICATIONS

*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Defendants' Third Supp'l Answers & Objections to Plaintiff's First Set of Interrogatories Nos. 1-6, Oct. 15, 2007.

In The United States Patent and Trademark Office, "Notice of Intent to Issue Ex Parte Reexamination Certificate," Ex Parte Reexamination No. 90/010,655 and No. 90/009,542, Filed Aug. 24, 2009 and Jul. 24, 2009, date mailed Jul. 14, 2010, 9 pages.

In The United States Patent and Trademark Office, "Patent Owner's Response Pursuant to 37 C.F.R. § 1.550 in Merged Ex Parte Reexamination of U.S. Patent No. 6,936,071," Ex Parte Reexamination No. 90/010,655 and No. 90/009,542, Filed Aug. 24, 2009 and Jul. 24, 2009, dated May 19, 2010, 36 pages.

In The United States Patent and Trademark Office, "Request for Ex Parte Reexamination," In re patent of: Marnay et al., U.S. patent # 6,936,071, filed on Jul. 24, 2009, 70 pages.

In The United States Patent and Trademark Office, "Request for Ex Parte Reexamination," in re patent of: Marnay et al., U.S. patent # 6,936,071, filed on Aug. 24, 2009, 23 pages.

"Appeal from the US District Court: *Spine Solutions, Inc.* vs. *Medtronic Sofamor Danek USA, Inc.*", In The United States Court for the Western District of Tennessee, Case No. 07-CV-02175, Decided: Sep. 9, 2010, 28 pages.

"Amended Judgment Awarding Enhanced Damages, Prejudgment Interest and Attorney Fees", Filed Nov. 9, 2009, Doc. 521, 2 pages.

"Amended Order Denying Defendants' Motion for Summary Judgment of Invalidity Under 35 U.S.C. § 103", Dated Nov. 6, 2008, Doc. 332, 20 pages.

"Amended Order Denying Medtronic's Renewed Motion for Judgment as a Matter of Law and Alternative Motion for a New Trial", Filed Aug. 20, 2009, doc. 494, 30 pages.

"Judgment Awarding Enhanced Damages, Post-Dec. 31, 2007 Damages, Pre- and Post-Judgment Interest, and Injunctive Relief", Filed Aug. 26, 2009, Doc. 497, 2 pages.

"Order Amending and Altering the Judgment Entered on Aug. 26, 2009 to Alter the Amount of Damages and Interest Awarded and to Amend the Judgment to Provide for an Award of Attorney Fees", Filed Nov. 9, 2009, Doc. 520, 20 pages.

(56) References Cited

OTHER PUBLICATIONS

"Order Denying Defendants' Motion for Summary Judgment of Invalidity under 35 U.S.C. § 103", Dated Sep. 30, 2008, Doc. 317, 20 pages.
"Order Denying Defendants' Motion for Summary Judgment of No Willful Infringement", Dated Sep. 30, 2008, Doc. 318, 12 pages.
"Order Denying Defendants' Motion for Summary Judgment of Non-infringement on 0-MAV; Order Granting Plaintiff Spine Solutions, Inc.'s Motion for Partial Summary Judgment of Infringement of Claims 1 and 2 of U.S. Patent No. 6,939,071", Dated Sep. 30, 2008, Doc. 313, 14 pages.
"Order Denying Defendants' Motion for Summary Judgment of Non-infringement, or in the Alternative for Invalidity; Order Granting Plaintiff Spine Solutions, Inc.'s Motion for Partial Summary Judgment Dismissing Medtronic's 35 U.S.C. §112 Defenses", Dated Sep. 30, 2008, Doc. 314, 16 pages.
English Abstract, DE 3526742 A1, Jansson, Jan. 29, 1987.
In the United States Patent and Trademark Office, in Re. U.S. Appl. No. 10/070,823, filed Jul. 15, 2002 Notice of Allowance mailed Jul. 24, 2006.
In the United States Patent and Trademark Office, in Re. U.S. Appl. No. 10/070,823, filed Jul. 15, 2002, Examiner Interview Summary Record and Notice of Allowance mailed Jul. 13, 2006.
In the United States Patent and Trademark Office, in Re. U.S. Appl. No. 10/070,823, filed Jul. 15, 2002, Final Rejection mailed Aug. 23, 2005.
In the United States Patent and Trademark Office, in Re. U.S. Appl. No. 10/070,823, filed Jul. 15, 2002, Non-Final Office Action, mailed Sep. 23, 2004.
In the United States Patent and Trademark Office, in Re. U.S. Appl. No. 10/318,078, filed Dec. 13, 2002, Issue Notice mailed Mar. 28, 2007.
In the United States Patent and Trademark Office, in Re. U.S. Appl. No. 10/318,078, filed Dec. 13, 2002, Notice of Allowance mailed Feb. 26, 2007.
In the United States Patent and Trademark Office, in Re. U.S. Appl. No. 10/318,078, filed Dec. 13, 2002, Final Rejection mailed Aug. 1, 2006.
In the United States Patent and Trademark Office, in Re. U.S. Appl. No. 10/318,078, filed Dec. 13, 2002, Final Rejection mailed Nov. 12, 2004.
In the United States Patent and Trademark Office, in Re. U.S. Appl. No. 10/318,078, filed Dec. 13, 2002, Non-Final Office Action mailed Apr. 21, 2004.
In the United States Patent and Trademark Office, in Re. U.S. Appl. No. 10/318,078, filed Dec. 13, 2002, Non-Final Office Action mailed Aug. 8, 2005.
In the United States Patent and Trademark Office, In Re. U.S. Appl. No. 10/622,535 filed Jul. 21, 2003: Non Final Office Action mailed Apr. 26, 2007.
In the United States Patent and Trademark Office, In Re. U.S. Appl. No. 10/622,535 filed Jul. 21, 2003: Non Final Office Action mailed Aug. 30, 2005.
In the United States Patent and Trademark Office, In Re. U.S. Appl. No. 10/622,535 filed Jul. 21, 2003: Non Final Office Action mailed Feb. 6, 2009.
In the United States Patent and Trademark Office, In Re. U.S. Appl. No. 10/622,535 filed Jul. 21, 2003: Non Final Office Action mailed Jan. 31, 2008.
In the United States Patent and Trademark Office, In Re. U.S. Appl. No. 10/622,535 filed Jul. 21, 2003: Non Final Office Action mailed Nov. 8, 2006.
In the United States Patent and Trademark Office, In Re. U.S. Appl. No. 10/622,535 filed Jul. 21, 2003: Non Final Office Action mailed Sep. 12, 2007.
In the United States Patent and Trademark Office, In Re. U.S. Appl. No. 10/622,535 filed Jul. 21, 2003: Notice of Allowance mailed Jul. 20, 2009.
In the United States Patent and Trademark Office, In Re. U.S. Appl. No. 10/622,535 filed Jul. 21, 2003: Final Rejection mailed May 23, 2006.
In the United States Patent and Trademark Office, In Re. U.S. Appl. No. 10/622,535 filed Jul. 21, 2003: Notice of Allowance mailed Nov. 17, 2009.
In the United States Patent and Trademark Office, In Re. U.S. Appl. No. 11/512,327 filed Aug. 30, 2006: Notice of Allowance mailed Oct. 8, 2009.
In the United States Patent and Trademark Office, In Re. U.S. Appl. No. 11/512,327, filed Aug. 30, 2006, Final Rejection mailed Jun. 23, 2009.
In the United States Patent and Trademark Office, In Re. U.S. Appl. No. 11/512,327, filed Aug. 30, 2006, Non Final Rejection mailed Oct. 6, 2008.
"Brief in Support of Medtronic's Motion for Judgment as a Matter of Law on the Obviousness of the '071 Patent, no Willful Infringement and no Lost Profits" (Dec. 4, 2008, Doc. 406), *Spine Solutions, Inc.* v. *Medtronic Sofamor Danek, Inc. et al.*, U.S. District Court, Western District of Tennessee, Civil Docket #2:07-cv-02175-JPM-dkv.
"Citation of Supplemental Authority in Support of Medtronic's Renewed Motion for Judgment as a Matter of Law and Alternative Motion for a New Trial," with accompanying exhibit (Feb. 18, 2009, Docs. 453, 453-2), *Spine Solutions, Inc.* v. *Medtronic Sofamor Danek, Inc. et al.*, U.S. District Court, Western District of Tennessee, Civil Docket #2:07-cv-02175-JPM-dkv.
"Judgment" (Dec. 8, 2008, Doc. 412), *Spine Solutions, Inc.* v. *Medtronic Sofamor Danek, Inc. et al.*, U.S. District Court, Western District of Tennessee, Civil Docket #2:07-cv-02175-JPM-dkv.
"Jury Verdict Form" (Dec. 5, 2008, Doc. 411), *Spine Solutions, Inc.* v. *Medtronic Sofamor Danek, Inc. et al.*, U.S. District Court, Western District of Tennessee, Civil Docket #2:07-cv-02175-JPM-dkv.
"Memorandum in Support of Medtronic's Renewed Motion for Judgment as a Matter of Law and Alternative Motion for a New Trial," with accompanying exhibits (Dec. 22, 2008, Docs. 420-2 through 420-22), *Spine Solutions, Inc.* v. *Medtronic Sofamor Danek, Inc. et al.*, U.S. District Court, Western District of Tennessee, Civil Docket #2:07-cv-02175-JPM-dkv.
"Memorandum in Support of Plaintiffs' Motion for Judgment as a Matter of Law that the '071 Patent is Not Invalid for Obviousness" (Dec. 4, 2008, Doc. 407 2), *Spine Solutions, Inc.* v. *Medtronic Sofamor Danek, Inc. et al.*, U.S. District Court, Western District of Tennessee, Civil Docket #2:07-cv-02175-JPM-dkv.
"Plaintiffs' Memorandum in Opposition to Medtronic's Renewed Motion for Judgment as a Matter of Law and Alternative Motion for a New Trial" (Jan. 23, 2009, Doc. 439), *Spine Solutions, Inc.* v. *Medtronic Sofamor Danek, Inc. et al.*, U.S. District Court, Western District of Tennessee, Civil Docket #2:07-cv-02175-JPM-dkv.
"Plaintiffs' Memorandum in Response to Medtronic's Reply Memorandum and Citation of Supplemental Authority, Regarding Medtronic's Renewed Motion for Judgment as a Matter of Law and Alternative Motion for a New Trial" (Mar. 11, 2009, Doc. 463), *Spine Solutions, Inc.* v. *Medtronic Sofamor Danek, Inc. et al.*, U.S. District Court, Western District of Tennessee, Civil Docket #2:07-cv-02175-JPM-dkv.
"Reply Memorandum in Support of Medtronic's Renewed Motion for Judgment as a Matter of Law and Alternative Motion for a New Trial," with accompanying exhibit (Feb. 10, 2009, Docs. 449, 449-2), *Spine Solutions, Inc.* v. *Medtronic Sofamor Danek, Inc. et al.*, U.S. District Court, Western District of Tennessee, Civil Docket #2:07-cv-02175-JPM-dkv.
Ahrens et al., "Normal Joint Mobility is Maintained With an Artificial Disc Prosthesis," W Link, 1999.
David S. Hungerford, M.D. and Robert V. Kenna, "Preliminary Experience with a Total Knee Prosthesis with Porous Coating Used without Cement," Clinical Orthopaedics and Related Research, Cementless Total Knee Prosthesis, No. 176, Jun. 1983.
Marnay, "L'Arthroplastie Intervertebrale Lombaire," La Revue de Medicine Orthopedique, Jun.-Sep., 1991, No. 25; pp. 48-55.
Marnay, "Lumbar Intervertebral Arthroplasty,".
Pacer Docket sheet from *Spine Solutions, Inc.* v. *Medtronic Sofamor Danek, Inc. et al.*, U.S. District Court, Western District of Tennessee, Civil Docket #2:07-cv-02175-JPM-dkv.

(56) References Cited

OTHER PUBLICATIONS

Robert E. Tooms, "Arthroplasty of ankle and knee," Campbell's Operative Orthopaedics, Seventh Edition, Volume Two, ed. A.H. Crenshaw, (St. Louis, Washington, D.C., Toronto: The C.V. Mosby Company 1987), 1145-1152.

Robert V. Kenna and David S. Hungerford, M.D., "Design Rational for the Porous Coated Anatomic Total Knee System," Total Knee Arthroplasty, a Comprehensive Approach, ed. David S. Hungerford, M.D., Kenneth A. Krackow, M.D., and Robert V. Kenna (Baltimore/London: Williams & Wilkins 1984), 71-88.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Amended Answer and Counterclaims, Nov. 21, 2007.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Answer and Counterclaims, May 4, 2007.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Defendants' Medtronic Sofamor Danek, Inc. and Medtronic Sofamor Danek USA, Inc.'s Sixth Supplemental Answers and Objections to Plaintiff's First Set of Interrogatories, Dec. 14, 2007.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Defendants' Opening Markman Brief, Feb. 19, 2008.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Defendants' Reply Markman Brief, Mar. 31, 2008.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Defendants' Responsive Markman Brief, Mar. 17, 2008.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Defendants' Supplemental Brief in Support of Their Motion for Summary Judgment of Invalidity Under 35 U.S.C. § 103, Jun. 19, 2008.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Expert Report #2, Rebuttal to other reports in this litigation, Paul Ducheyne, Ph.D. Dec. 21, 2007.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Expert Report of Charles A. Laff, Nov. 21, 2007.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Expert Report of Dr. Thomas A. Zdeblick, M.D., Nov. 21, 2007.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Expert Report of Mark E. Nusbaum, Nov. 21, 2007.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Expert Report of Stephen D. Cook, Ph.D., Nov. 21, 2007.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Order Following Markman Hearing, Jul. 2, 2008.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Plaintiff Spine Solutions' Responsive Markman Brief, Mar. 17, 2008.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Plaintiff Spine Solutions, Inc.'s Motion for Leave to File a Response to Defendants' Surreply Memorandum Regarding Plaintiff's Motion for Partial Summary Judgment of Failure of Defendants to State a Legal Defense or Claim for Relief based on Inequitable Conduct and a Declaration of Marvin Petry in Support Thereto, Jun. 25, 2008.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Plaintiff Spine Solutions, Inc.'s Motion for Leave to File a Surreply to Defendants' Reply Markman Brief, Apr. 7, 2008.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Plaintiff Spine Solutions, Inc.'s Reply Markman Brief, Mar. 31, 2008.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Plaintiff Spine Solutions, Inc.'s Reply Memorandum in Support of Motion for Partial Summary Judgment of Failure of Defendants to State a Legal Defense or Claim for Relief Based on Inequitable Conduct, Mar. 31, 2008.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Plaintiff Spine Solutions, Inc.'s Response to Defendants' Motion to Amend Their Answer to Allege Inequitable Condcut, Dec. 7, 2007.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Plaintiff's Supplemental Response to Defendants' Interrogatory No. 2 (Relating to Conception, Reduction to Practice, First Sale), Oct. 29, 2007.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Plantiff Spine Solutions, Inc.'s Opening Markman Brief, Feb. 19, 2008.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Rebuttal Expert Report of Mark E. Nusbaum, Dec. 21, 2007.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Reply Brief in Support of Plaintiff Spine Solutions, Inc.'s Motion for Patial Summary Judgment Dismissing Medtronic's 35 U.S.C. § 112 Defenses, Mar. 31, 2008.

Szpalski et al., "Spine arthroplasty: a historical review," Eur Spine J., 2002, 11(Suppl. 2), S65-S84 DOI 10.1007/s00586-002-0474-y.

The Journal of Bone and Joint Surgery, "A New Tibia Plateau", Jul. 1970, vol. 52-A, No. 5.

The Journal of Bone and Joint Surgery, "Here's a Good Skate", Sep. 1971, vol. 53-A, No. 6.

Transcript Pages: pp. 1441-1639, 1644-1682 (Dec. 3- 4, 2008), *Spine Solutions, Inc. v. Medtronic Sofamor Danek, Inc. et al.*, U.S. District Court, Western District of Tennessee, Civil Docket #2:07-cv-02175-JPM-dkv.

Transcript Pages: pp. 1842-1892, 1899-1944 (Dec. 4-5, 2008), *Spine Solutions, Inc. v. Medtronic Sofamor Danek, Inc. et al.*, U.S. District Court, Western District of Tennessee, Civil Docket #2:07-cv-02175-JPM-dkv.

Transcript Pages: pp. 345-535, 544-644, 669-700 (Nov. 25-26, 2008) *Spine Solutions, Inc. v. Medtronic Sofamor Danek, Inc. et al.*, U.S. District Court, Western District of Tennessee, Civil Docket #2:07-cv-02175-JPM-dkv.

Transcript Pages: pp. 908-1071, 1085-1102 (Dec. 1-2, 2008), *Spine Solutions, Inc. v. Medtronic Sofamor Danek, Inc. et al.*, U.S. District Court, Western District of Tennessee, Civil Docket #2:07-cv-02175-JPM-dkv.

Viscogliosi Brothers, LLC, "Spine Arthroplasty", Nov. 2001.

\* cited by examiner

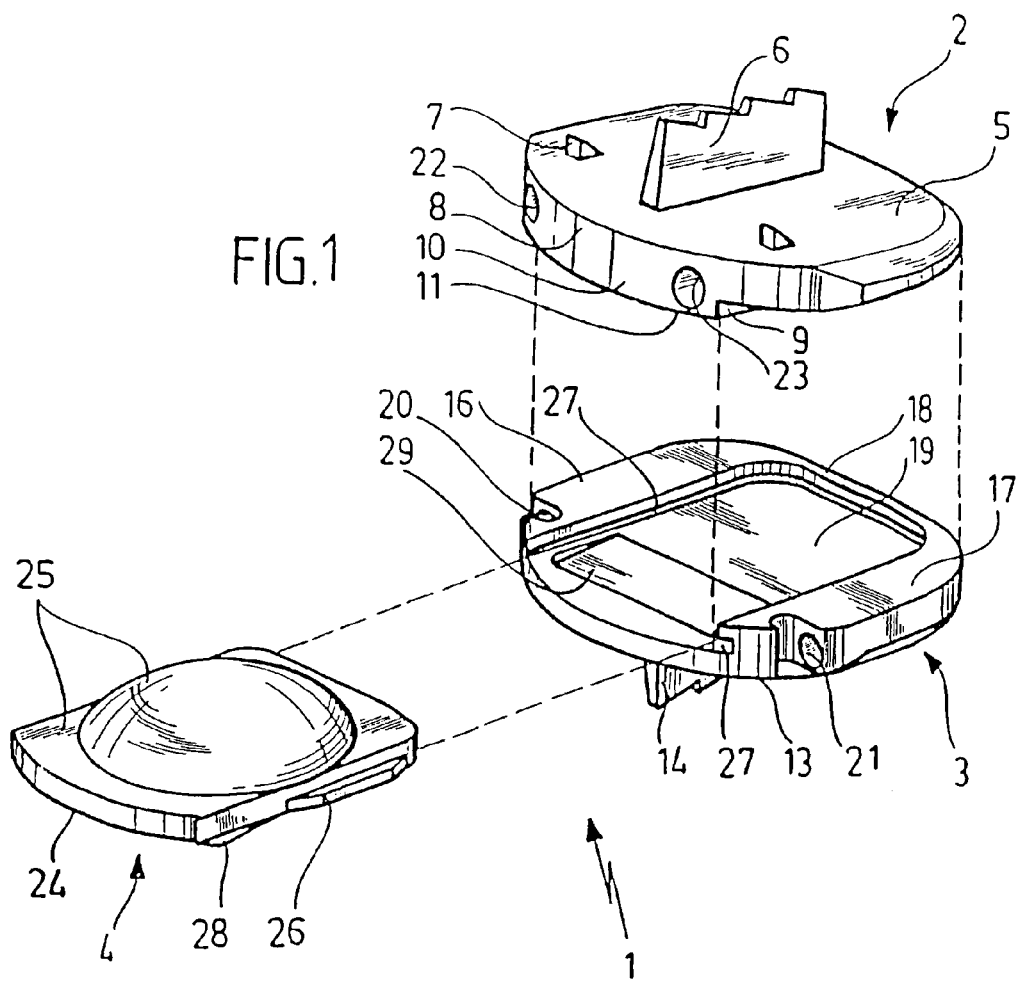

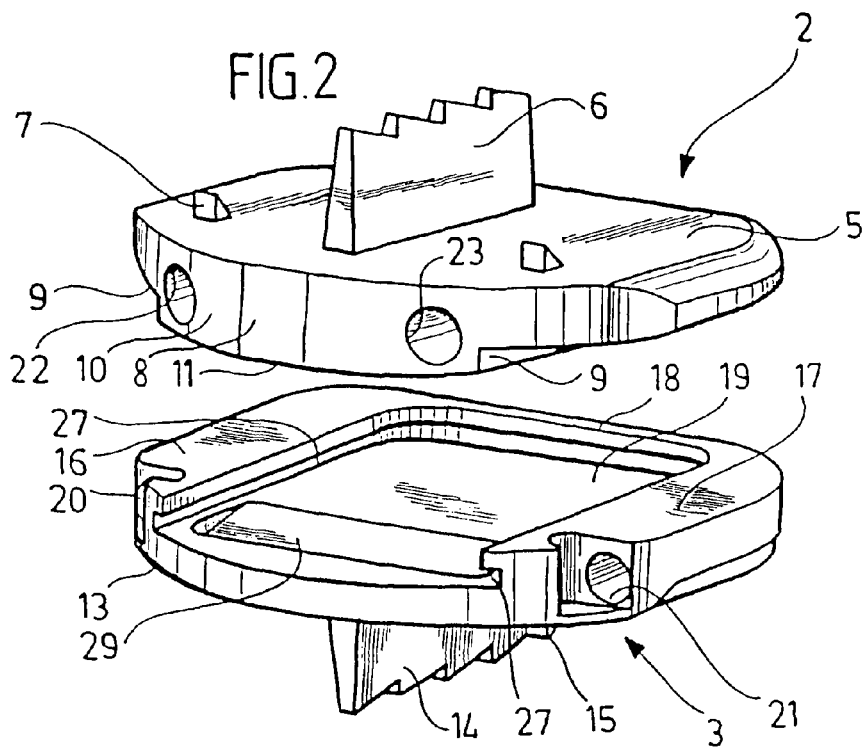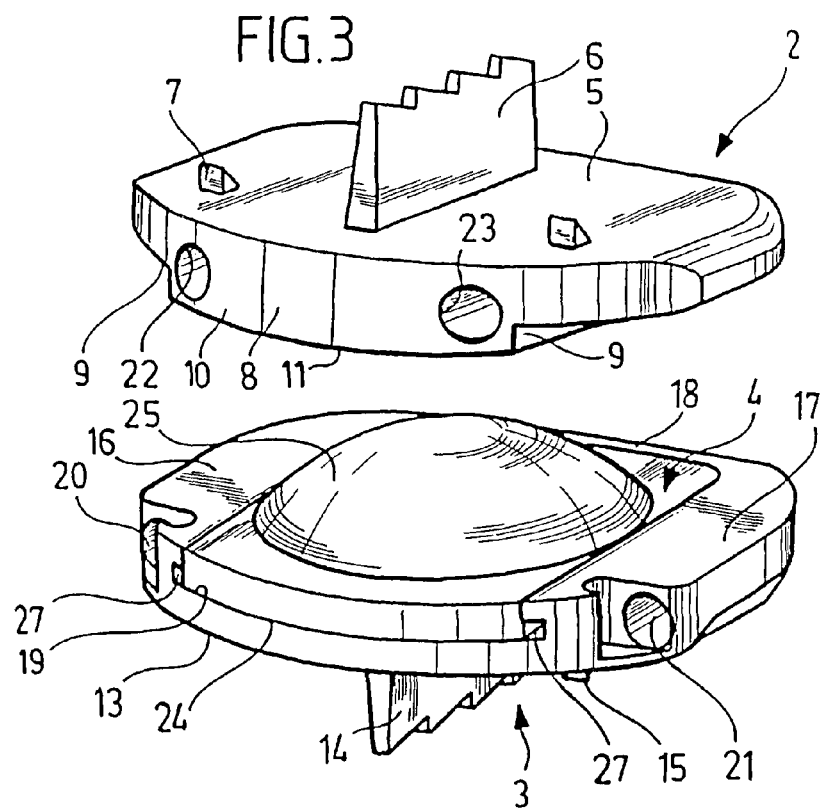

INTERVERTEBRAL IMPLANT

CROSS REFERENCE TO RELATED APPLICATIONS

This application is a continuation of U.S. application Ser. No. 10/998,951, filed Nov. 30, 2004, now U.S. Pat. No. 8,506,634, which is in turn a continuation of U.S. application Ser. No. 10/018,402, now U.S. Pat. No. 6,936,071, which was a national stage application based on International Application Serial No. PCT/EP99/04628, filed Jul. 2, 1999.

BACKGROUND OF THE INVENTION

The invention relates to an intervertebral implant, having an upper part that has a support face for a vertebra and a lower part that has a support face for an adjacent vertebra, on each of which parts engagement elements, which are accessible from one side of the intervertebral implant, for a manipulation instrument are disposed, in order to minimize the structural height of the intervertebral implant upon insertion into an intervertebral space.

One such intervertebral implant is known for instance from U.S. Pat. No. 5,314,477. This intervertebral implant is used to replace a disk removed from the intervertebral space, and accordingly the intervertebral implant must have a relatively low structural height, since it has to fit into the gap between vertebrae. This is particularly difficult if an additional pivot insert is also embedded between the upper part and the lower part, as is the case in the known intervertebral implant of U.S. Pat. No. 5,314,477.

But even in two-piece intervertebral implants, difficulties also arise, especially if the implants also have pins and other protrusions on their support faces that are intended for anchoring the intervertebral implant in the bone. Often, these parts can be inserted only by widening the intervertebral space greatly. Not only is this difficult, but it also presents the risk of injuries.

Since the intervertebral space has a relatively low height, it is also difficult for engagement elements that a manipulation instrument can engage to be secured to both parts of the intervertebral implant. It is conventional to have such manipulation instruments engage the upper part and the lower part separately, for instance by means of pins that are inserted into bores on the upper part and lower part, so that with the manipulation instrument, the two parts of the intervertebral implant can be inserted into the intervertebral space and can optionally also be varied in terms of their spacing from one another, thereby allowing a certain spreading open of the intervertebral space. In this respect, reference is made to the pincerlike manipulation instrument of U.S. Pat. No. 5,314,477.

Because of the strong forces, it is necessary to provide a certain structural height for the engagement elements; for instance, the receiving bores must have a certain diameter. This dictates a minimum structural height for the upper part and for the lower part, and in conventional intervertebral implants, the structural heights of the upper part and lower part are thus added together, so that even if the upper and lower parts rest directly on one another, a relatively great structural height of the intervertebral implant is still unavoidable.

SUMMARY OF THE INVENTION

It is the object of the invention to embody an intervertebral implant of this generic type in such a way that the minimum structural height is reduced, to make it easier to insert the intervertebral implant into the intervertebral space.

In an intervertebral implant of the type described at the outset, this object is attained in accordance with the invention in that it is proposed that the upper part and lower part each have protrusions and recesses aimed at the respectively other part, which are offset laterally from one another in such a way that when the upper part has been brought close to the lower part they mesh with one another; and that the engagement elements on the upper part and on the lower part are each disposed in protrusions of these parts in such a way that the engagement elements of the upper part and lower part are located side by side and at least partly overlap in the direction of the height of the intervertebral implant.

In such an embodiment, a minimal structural height of the two intervertebral implant parts resting on one another can be attained, since the engagement elements, which cannot fall below a minimal structural height, are each disposed in protrusions of the upper part and lower part, or in other words in the parts of the upper part and lower part that have the greatest structural height. These regions of great structural height are embodied as protrusions, next to which are respective recesses, into which the protrusions of the respectively other part can dip. As a result, on the one hand, the engagement elements for the manipulation instruments are located side by side, and on the other, they can at least partly overlap, so that the total structural height of the parts resting on one another of the intervertebral implant can be reduced markedly compared to conventional intervertebral implants. The result is accordingly an internested arrangement of the upper and lower parts, with maximal exploitation of the available material height.

It is favorable if the engagement elements are insertion openings for pinlike retaining elements of a manipulation instrument; because of the described construction, these insertion openings can have a relatively large diameter and can thus receive strong retaining pins, and nevertheless a relatively low structural height of the intervertebral implant with parts resting directly on one another is obtained.

It is advantageous if the insertion openings extend substantially parallel to the support faces; once again, this prevents an increase in the structural height of the intervertebral implant parts.

In a preferred embodiment, it is provided that the lower part has a central indentation, opposite the lower support face, which indentation is surrounded by a U-shaped edge. Thus with the lower part and upper part resting directly on one another, the indentation serves to receive a protrusion on the upper part.

It is advantageous if the upper part has a central protrusion that fits substantially in complimentary fashion into the indentation; that is, the total volume of the indentation is utilized for the protrusion.

It is also advantageous if the engagement elements of the lower part are disposed on the two ends of the U-shaped edge, or in other words are located on the outside.

Conversely, the engagement elements of the upper part can be disposed on the central protrusion of the upper part, or in other words are located farther inward than the engagement elements of the upper part.

In particular, the engagement elements of the upper part can be disposed near the lateral edges of the central protrusion, so that for the upper part as well, the spacing of the engagement elements can be selected to be relatively great; as a result, both the upper part and the lower part can be reliably secured against skewing.

It should already be noted here that the words "lower part" and "upper part" do not necessarily say anything about the installed position of the intervertebral implant in the spinal column; the part called the "lower part" could in fact be above in the spinal column. Therefore, these parts may also be referred to as first and second parts having outer and inner surfaces. What is essential is merely that the upper part and lower part define the intervertebral implant on opposite sides of the implant.

It is especially advantageous if the upper part and/or the lower part is embodied in substantially platelike fashion; these parts naturally, in accordance with the design of the invention, have protrusions and recesses that are oriented toward the respectively other part. The platelike embodiment, however, leads as a whole to a very low structural height of the intervertebral implant.

In a preferred embodiment, the lower part and the upper part each have a respective receptacle for a pivot insert. This pivot insert, which is placed between the upper part and lower part after the insertion of the intervertebral implant, supports the upper part and lower part against one another; it takes on a resilient function, for instance, and furthermore leads to a certain pivotability of the two parts of an intervertebral implant relative to one another, so that a pivotability of the adjacent vertebra is thus attainable as well.

In particular, it is advantageous if the pivot insert has at least one spherical support face, which engages the correspondingly spherically shaped receptacle.

It is favorable if the spherical receptacle is disposed in the central protrusion of the upper part.

It is also advantageous if the central indentation of the lower part forms the receptacle for the pivot insert.

According to a preferred embodiment of the invention, it is provided that the pivot insert can be inserted from the side into the receptacle, which has the engagement elements for a manipulation instrument. This is the side from which the upper part and lower part are introduced into the intervertebral space, and it is also from this side that the pivot insert can then be thrust between the already-inserted parts of the intervertebral implant.

It is favorable if the pivot insert is insertable into the receptacle along a guide.

In that the insert as well is preferably embodied substantially in platelike fashion.

An especially favorable design is obtained if the insert substantially completely fills up the central receptacle and with its spherical support face protrudes from the receptacle.

BRIEF DESCRIPTION OF THE DRAWINGS

The ensuing description of preferred embodiments of the invention serves in conjunction with the drawing to provide further explanation. Shown are:

FIG. 1: a perspective exploded view of an intervertebral implant with an upper part, a lower part, and a pivot insert that can be inserted between them;

FIG. 2: a perspective exploded view of the upper part and the lower part of the intervertebral implant, without an inserted pivot insert;

FIG. 3: a view similar to FIG. 2 with the pivot insert inserted into the lower part;

DETAILED DESCRIPTION OF THE PREFERRED EMBODIMENTS

Figure 4:
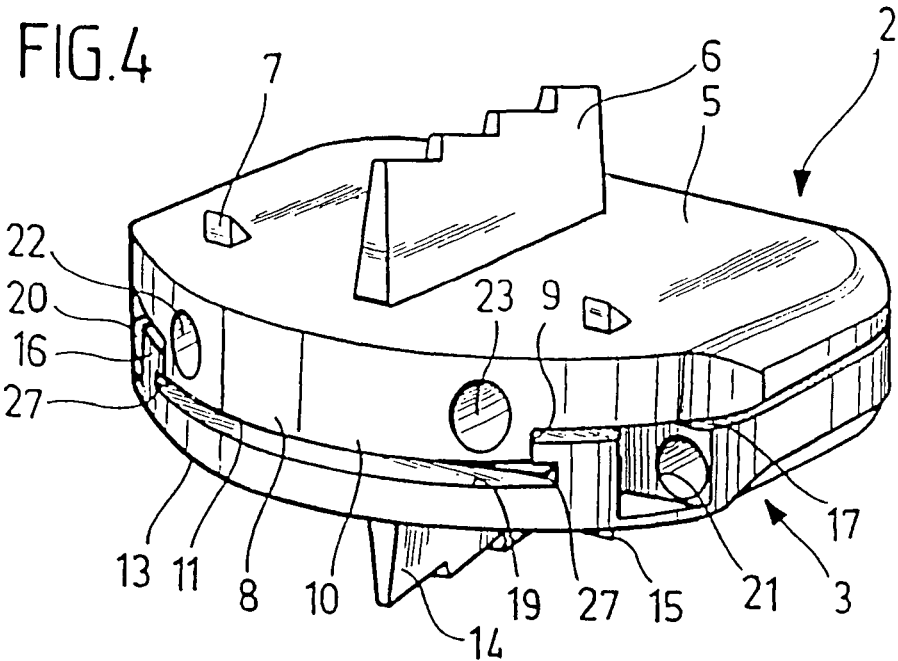
FIG. 4: a perspective view of the upper part and the lower part of the intervertebral implant with maximum mutual proximity.

The intervertebral implant 1 shown in the drawing includes three parts, namely a platelike upper part 2, a platelike lower part 3, and a substantially platelike pivot insert 4. In plan view, the implant, although having rounded corners, is generally rectangular.

The upper part 2 is embodied flat on its top, thus creating a support face 5, on which various kinds of protrusions 6, 7 are disposed which serve the purpose of anchoring the upper part 2 in a vertebra that rests, with its end face toward an intervertebral space, on the support face 5. As is most evident from FIG. 5, the height of each smaller protrusion 7 is not greater than its width.

The upper part 2 is substantially rectangular in cross section; in the exemplary embodiment shown, a longitudinal edge 8 curves outward.

On the two short sides of this rectangle, the thickness of the platelike upper part 2 is less than in the central region, so that along the short sides of the upper part 2, downward-pointing recesses 9 each extending parallel to these edges are formed that are open toward the outside. The central region of the upper part 2 is located between the two recesses 9 and thus has a greater thickness or height and thus forms a downward-pointing protrusion 10 embodied between the two recesses 9. This protrusion is defined by an underside 11, which extends substantially parallel to the support face 5 and in which there is a spherical indentation 12, which forms a bearing plate for the pivot insert 4.

The lower part 3 of the intervertebral implant 1 is also platelike in embodiment and on its underside has a flat support face 13 with protrusions 14 and 15, which correspond to the protrusions 6 and 7 of the support face 5. On the side remote from the support face 13, the thickness of the lower part 3 is less in the central region than in an outer region. This outer region of greater thickness has the form of a U, with two parallel legs 16, 17, which extend parallel to the short edges of the lower part 3, which in cross section is embodied similarly to the upper part 2, and with a crosspiece 18 that connects the two legs 16 and 17 on one end. The region enclosed by the legs 16 and 17 and the crosspiece 18 forms a central indentation 19, whose area is substantially equivalent to the area of the central protrusion 10 of the upper part 2, while the disposition and length of the legs 16 and 17 correspond essentially to the disposition and length of the recesses 9 on the upper part 2. As a result, it is possible to place the upper 2 and lower part 3 on one another in such a way that the central protrusion 10 of the upper 2 dips into the central indentation 19, while the legs 16 and 17 of the lower part 3 dip into the recesses 9 of the upper part 2 (FIG. 4); in this position, the upper part 2 and lower part 3 have maximum proximity to one another and a minimal structural height.

The dimensions are selected such that the various recesses are essentially filled completely by the protrusions dipping into them.

Blind bores 20 and 21 are machined into the two legs 16 and 17 of the lower part 3, extending parallel to these legs 16, 17 from their free ends; the diameter of these bores is relatively great in proportion to the height of the legs 16, 17, and this diameter is in fact greater than the thickness or height of the lower part 3 in the region of the central indentation 19.

Blind bores 22 and 23, which extend parallel to the blind bores 20 and 21 in the lower part 3, are machined into the central protrusion 10 of the upper part 2, in the vicinity of its side edges. These blind bores 22 and 23 again have a relatively great diameter, which corresponds to a substantial portion of the height of the protrusion 10 and is greater than the thickness of the upper part 2 in the region of the recesses 9.

Figure 5:
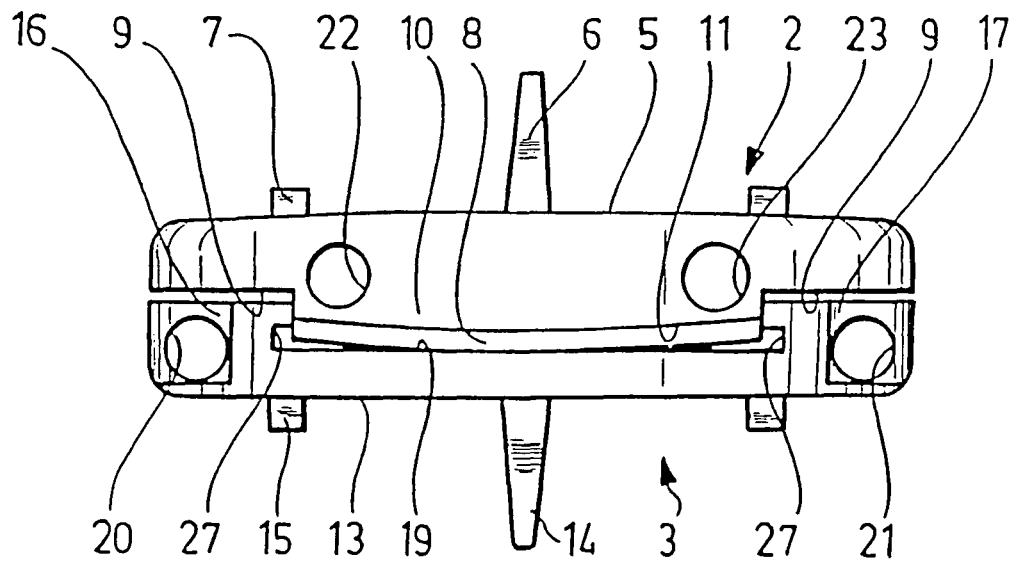
FIG. 5: a front view of the intervertebral implant of FIG. 4.

When the upper part 2 and lower part 3 rest tightly against one another in the manner described, the blind bores 20 and 21 of the lower part 3 and the blind bores 22 and 23 of the upper part 2 overlap at least partly in the direction of the height of the intervertebral implant 1, as is clearly shown in FIGS. 4 and 5.

The blind bores 20, 21, 22 and 23 serve as receptacles for pinlike extensions of a manipulation instrument, not shown in the drawing, and thus form engagement elements for this manipulation instrument, which in this way separately engages the upper part 2 and the lower part 3. With this manipulation instrument, it is possible to introduce the upper part 2 and the lower part 3 of the intervertebral implant 1 into an intervertebral space; the very low structural height of the intervertebral implant 1 facilitates this introduction, which can be done essentially without major widening of the intervertebral space.

After the introduction of the upper part 2 and lower part 3 in this way, the two parts of the intervertebral implant 1 can be spread apart; that is, their spacing is increased, for instance with the aid of the manipulation instrument that is holding the upper 2 and the lower part 3. Thus, in accordance with the method of operation, the upper and lower parts (or the first and second parts) are first inserted together into the intervertebral space, after which these parts are separated from each other and the insert is inserted between them. Thereafter, these parts are allowed to come together towards each other to engage the insert.

In this spread-open position of the upper part 2 and lower part 3, it is possible to thrust the pivot insert 4 between the upper part 2 and the lower part 3.

Figure 7:
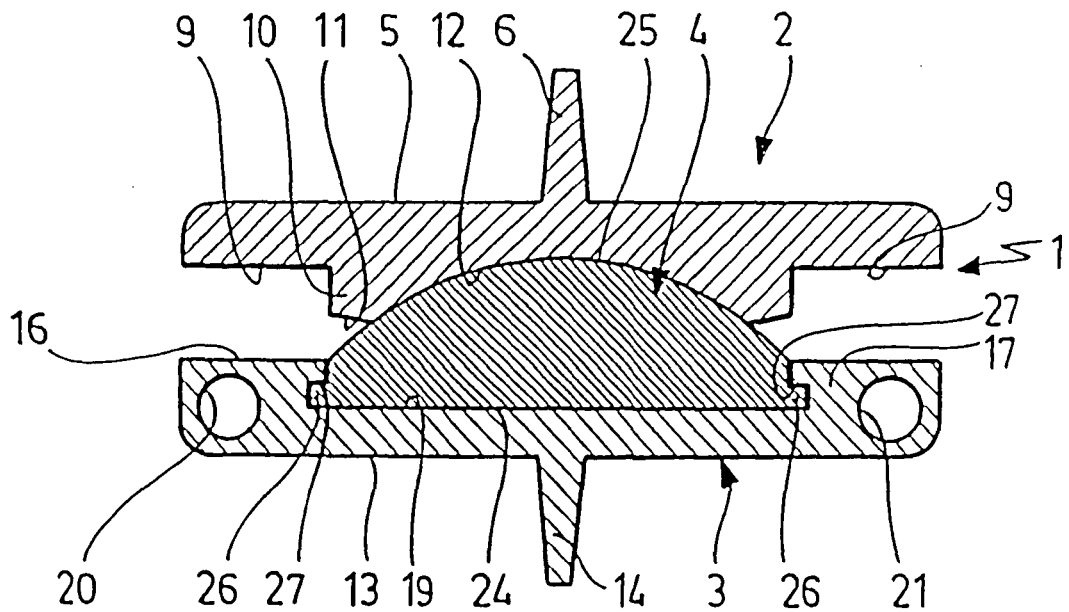
FIG. 7: a cross-sectional view of the intervertebral implant of FIG. 6.

This pivot insert is constructed essentially in the shape of a plate, which has a flat underside 24 and a spherically upward-curved top side 25. The outer dimensions of the platelike pivot insert correspond to those of the central indentation 19 in the lower part 3, so that the pivot insert 4 can be thrust into this indentation, filling it up, specifically from the side toward which the blind bores 20, 21, 22, 23 open. Guide strips 26 on the side edges of the pivot insert 4 engage corresponding guide grooves 27 in the legs 16, 17, so that an insertion guide for the pivot insert 4 is formed that fixes it in the lower part 3 after its insertion. The inserted pivot insert 4, after insertion, fills up the indentation 19 and protrudes with its spherically curved top side 25 upward past the top side of the lower part 3; the spherical top side 25 dips in complimentary fashion into the spherically curved indentation 12 on the underside of the protrusion 10, wherewith the upper part 2 it forms a ball joint, which enables a certain pivotability of the upper part 2 relative to the lower part 3 (FIG. 7).

The pivot insert 4 can have a detent protrusion 28 on its flat underside 24; when the pivot insert 4 is inserted into the lower part 3, this protrusion locks elastically into a detent recess 29 that is located on the bottom of the indentation 19; as a result, the pivot insert 4 is also fixed in the insertion direction in the indentation 19.

The upper part 2 and lower part 3 are preferably made of physiologically safe metal, such as titanium, while the pivot insert 4 preferably comprises a likewise physiologically safe plastic material, such as polyethylene. These support faces 5 and 13 can be embodied in an especially bone-compatible way; for instance, this surface can be roughened by a coating, so that optimal anchoring to the adjacent bone material is obtained.

The invention may also be described as follows, which description is the full equivalent of the preceding discussion. An upper part 2 has an upper surface 5 for engaging a vertebrae and a lower surface which comprises a downward pointing protrusion 10 between side recesses 9 and a rounded portion, preferably in the form of a concave spherical indentation 12. A lower part 3 has a lower surface 13 for engaging a vertebrae. A pivot insert 4, when joined to the lower part 3, as shown for example in FIG. 3, provides a convex upper surface portion 25, preferably spherical, in operational engagement with the rounded portion 12 of the upper part.

The lower part 3 and pivot insert 4 may, taken together, be described as a lower part formed in two pieces, namely the elements 3 and 4, wherein the element 3 may be referred to as a lower piece and the element 4 may be referred to as an upper piece.

The upper and lower parts include on their upper surface and lower surface, respectively, protrusions 6 and 14 which may also be referred to as anchors, which anchor the upper and lower parts, respectively, into the adjacent vertebrae that form the intervertebral space and rest against the respective upper and lower surfaces.

Figure 6:
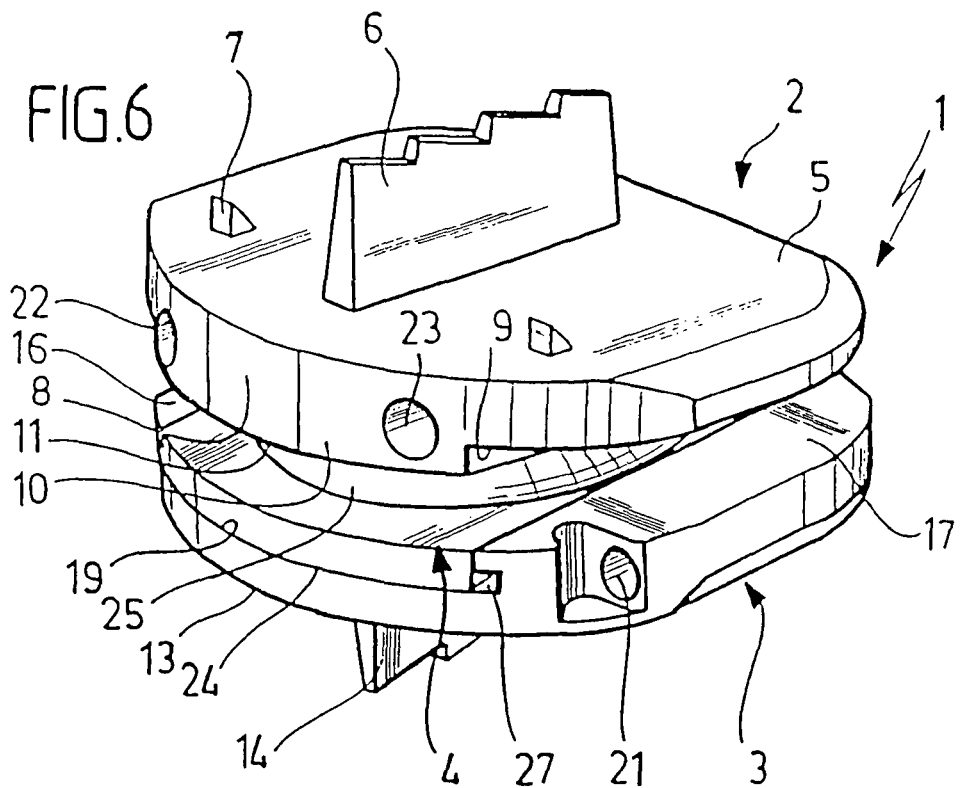
FIG. 6: a perspective view of the intervertebral implant with the pivot insert inserted.

As shown in the figures, the anchors 6 and 14 are each single anchors, preferably extending perpendicular to the respective outer surfaces from which they extend. The anchors may also be referred to as anchor portions and the plane or line along which the anchor or anchor portions extend may be referred to as an anchor line. Each of the anchors 6 and 14 has a zigzag edge which comprises a series of teeth. As best shown in the cross-sectional view of FIG. 7, anchor 6 has at least one section that is greater in height than the remainder of the upper part 2, i.e., from surface 5 to the bottom of protrusion 10, at the section of the upper part where the anchor section meets the surface of the part. Similarly, at least one section of anchor 14 is greater in height than the remainder of the lower part 3 exclusive of its convex portion, i.e., from lower surface 13 to the top of walls 16, 17 and 18. As can be seen from the perspective view of these same parts shown in FIG. 6, anchor 6 is aligned along a single anchor line across surface 5 to form a single anchor plane, this anchor plane having an anchor plane height at least a portion of which is greater than the height of the remainder of the upper part 2 at the section of the upper part where the anchor plane portion meets the surface. Alternatively, or additionally, as best shown in the front view of the parts depicted in FIG. 5, at least a portion (here, at least the facing portion) of anchor 6 is at least substantially equal in height to the overall height of the remainder of the upper part 2, i.e., from surface 5 to the bottom of protrusion 10 with its longitudinal edge 8. Furthermore, as can be seen in the perspective view of these same parts shown in FIG. 4, by virtue of the sloping edge of the anchor 6 at least a portion of the anchor plane height of anchor 6 may be less than the overall height of the remainder of the upper part 2. As also shown in the figures, in the preferred embodiment, the length of the anchors 6 and 14, i.e., in the direction from the anterior to the posterior thereof, is greater than one half of the overall dimension of its respective part from its anterior to its posterior (as defined with reference to the part's anterior posterior orientation in the body upon implantation), passing through that anchor. As also noted in the figures, the vertical height of each anchor 6 and 14 is greater than its width which is the dimension taken horizontally in FIG. 5 or 7. Furthermore, in the illustrated embodiment as shown in FIGS. 5 and 7 the anchors 6 and 14 lie essentially in a common vertical plane in the assembled implant. As best shown in FIG. 7, pivot insert 4 enables a certain pivotability, or articulating motion, of the upper part 2 relative to the lower part 3. Midlines are lines on the outer surfaces passing essentially through the center of the outer surfaces of parts 2 and 3. Such midlines may divide the part into two separate symmetrical halves. In the illustrated embodiment, the common vertical plane of anchors 6 and 14 is located essentially at a midline of the implant which lies in an anterior to posterior plane of the implant, again as defined with reference to the intended orientation of the implant upon implantation. Each anchor 6 and 14 is elongated along the anterior to posterior midline and the width of each anchor straddles the midline.

The lower part comprises three walls including parallel side walls 16 and 17 and a rear wall 18. These walls form between them a central indentation 19 which comprises a recess with a generally flat surface. The fourth side of the recess is open. The pivot insert 4 has a detent 28 that snap-fits into a detent recess 29 formed in the generally flat surface of recess 19.

As best shown in FIGS. 2, 4 and 5, in the absence of pivot insert 4, the protrusion 10 of upper part 2 can fit down between walls 16, 17 and 18 of the lower part 2. This fitting of protrusion 10 within the recess 19, surrounded by walls 16, 17 and 18 may be referred to as "nesting" since the protrusion 10 essentially "nests" within recess 19. With the upper and lower parts in this nested condition, as shown in FIGS. 4 and 5, the combined height of the upper and lower parts 2 and 3, i.e., the height from surface 13 to surface 5, is less than the total additive height of the upper and lower parts, taken separately, i.e., less than the total of the height from surface 13 to the top of walls 16, 17 and 18 plus the height from surface 5 to the bottom of protrusion 10.

To reach its final destination within an intervertebral space, the implant must of course be moved along a path, i.e., an insertion direction from outside of the patient, into the patient, and then into the intervertebral space. In the illustrated embodiment, as described above, instruments would engage apertures 20, 21, 22 and 23 to move implant along a path in an insertion direction. The anchors 6 and 14 are parallel to this path and each defines a single anchor line parallel to this path as the implant is moved into an intervertebral space. Each anchor is thus adapted to enter a corresponding groove in the adjacent vertebra as the implant is inserted. As a point of reference, lateral planes parallel to the direction of this path pass through the outermost boundaries of the implant which, in the preferred embodiment, would be the opposed side surfaces of the parts. Each anchor 6 and 14 lies at a midline at the center of the outer surface of each part 2 and 3 in between and parallel to the lateral parallel planes. Thus, in the illustrated embodiment, the path would be parallel to the front to rear (anterior to posterior) direction, wherein, during insertion, the rear (posterior) of the implant would constitute the lead end and the front (anterior) thereof would constitute the trailing end.

Although the invention has been described in detail with respect to preferred embodiments thereof, it will be apparent that the invention is capable of numerous modifications and variations, apparent to those skilled in the art, without departing from the spirit and scope of the invention.

The invention claimed is:

1. An intervertebral implant configured to be inserted into an intervertebral space between a first vertebra and a second vertebra, the intervertebral implant having a height extending in a first direction, a width extending in a second direction, and a depth extending in a third direction from a front end that leads into the intervertebral space upon insertion to a rear end opposite the front end, wherein the first, second, and third directions are each perpendicular to each other, comprising:

a first part having a first support face facing in the first direction for engaging the first vertebra and a downward pointing protrusion having opposing protrusion side walls with protrusion side wall surfaces extending in the third direction and the first part having an inner surface oppositely facing the first support face and the inner surface of the first part having a spherically curved indentation;

a second part having a second support face facing oppositely the first support face for engaging the second vertebra, a rear wall, and a central indentation opposite the second support face, the central indentation partially formed between two opposing inner surfaces of two side walls extending in the third direction, the second part further having an inner surface of a front wall adjacent the front end, the inner surfaces of the side walls and front wall each extending up from a bottom surface facing the first direction and opposite the second support face, the central indentation also including a side opening located at the rear wall of the second part, the downward pointing protrusion of the first part being positionable within the central indentation in a nested condition, such that a combined height of the first and second parts in the nested condition is less than an additive height of the first and second parts separately, and the protrusion side wall surfaces and the inner surfaces of the two side walls of the second part are designed to be parallel when the first and second parts are in the nested condition;

an insert having a spherically curved top side for engaging the spherically curved indentation of the first part in an installed position, the insert being insertable into the central indentation through the side opening; and wherein the first part has a midline on an outer surface of the first part and the second part has a midline on an outer surface of the second part, the midlines extending parallel to the third direction and passing essentially midway across the width of the outer surfaces and being generally parallel to each other, the first part having a first anchor on the midline of the first part and the second part having a second anchor on the midline of the second part, the first and second anchors having a height in the first direction, a length in the third direction, and a width in the second direction, wherein the height and the length of the first anchor being greater than the width of the first anchor and the height and the length of the second anchor being greater that the width of the second anchor.

2. The intervertebral implant of claim 1, further comprising:

guide grooves in the side walls of the second part facing into the central indentation; and the insert further comprising a bottom side oppositely facing the spherically curved top side, a first side and a second side both connecting the insert bottom side to the spherically curved top side, and guide strips extending from the first and second sides of the insert, the guide strips adapted to engage the guide grooves.

3. The intervertebral implant of claim 2, wherein the insert includes a detent protrusion and the bottom surface of the second part includes a detent recess, the detent protrusion positionable in the detent recess.

4. The intervertebral implant of claim 1, further comprising:
  one blind bore extending into each side wall of the second part.

5. The intervertebral implant of claim 1, further comprising:
  two blind bores extending into the downward pointing protrusion at a rear end of the first part.

6. An intervertebral implant configured and dimensioned to replace a disc removed from an intervertebral space and insertable between a superior vertebra and an adjacent inferior vertebra, the intervertebral implant having a height in a first direction, a width in a second direction, and a depth in a third direction, the first, second, and third directions being perpendicular to each other, the width of the intervertebral implant being greater than the depth, the intervertebral implant comprising:
  a first part having a substantially planar outer surface facing in the first direction configured to engage the superior vertebra and an inner surface facing oppositely the substantially planar outer surface, the inner surface including a concave portion, the first part outer surface having a front edge and a back edge located opposite the front edge, the first part having a first depth in the third direction between the front and back edges;
  a second part having an outer surface facing oppositely the first part outer surface configured to engage the inferior vertebra, an inner surface facing in the first direction and having a spherical portion adapted to operatively engage the concave portion of the first part, a sidewall located between and connecting the second part outer surface and second part inner surface, and the second part inner surface having a second portion not adapted to operatively engage the concave portion of the first part, the second portion located between the second part sidewall and the spherical portion;
  the intervertebral implant being constructed to be a sole implant in the intervertebral space;
  the intervertebral implant having lateral planes extending in the first and third directions and passing through outermost boundaries of the width of the intervertebral implant, and a midline on the outer surface of each of the first and second parts where the midline extends in the third direction essentially midway between the lateral planes, and
  an anchor on each of the outer surface of the first part and the outer surface of the second part, each said anchor having a height in the first direction, a length extending along the midline, and a width perpendicular to the height and the length, wherein each said anchor has a maximum height at a first position that is greater than a first width measured at the first position and a maximum length greater than the maximum height, each said anchor being adapted to enter a groove in one of the superior vertebra or the inferior vertebra as the intervertebral implant moves along a path into the intervertebral space, to anchor the first or second part to the superior vertebra or the inferior vertebra;
  wherein a first center height of the anchor on the outer surface of the first part at a center position located at approximately a center of the midline of the first part is greater than a height of a remainder of the first part measured between the outer surface and the inner surface of the first part at the center position and wherein the midline of the first part is the only location on the first part outer surface having an anchor having a height equating to the first center height.

7. An intervertebral implant configured and dimensioned to replace a disc removed from an intervertebral space and configured to be inserted into the intervertebral space between a first vertebra and an adjacent second vertebra, the intervertebral implant having a height in a first direction, a width in a second direction, and a depth in a third direction, the first, second, and third directions being perpendicular to each other, the width of the intervertebral implant being greater than the depth, the intervertebral implant comprising:
  a first part having a substantially planar outer surface facing in the first direction adapted to engage the first vertebra and an inner surface facing oppositely the outer surface that includes a concave portion, the first part outer surface having a front edge and a back edge located opposite the front edge, the first part having a first depth in the third direction between the front and back edges;
  a second part having a substantially planar outer surface facing oppositely the first part outer surface and adapted to engage the second vertebra, and an oppositely facing inner surface that has a spherical portion adapted to operatively engage the concave portion of the first part, a sidewall located between and connecting the second part outer surface and inner surface, and the second part inner surface having a second portion not adapted to operatively engage the concave portion of the first part where the second portion is located between the second part sidewall and the spherical portion;
  the first and second parts being adapted for engagement with each other;
  the intervertebral implant having a leading end that leads as the intervertebral implant is inserted along an insertion path into the intervertebral space and a trailing end opposite the leading end and lateral planes extending in the first direction and passing through outermost boundaries of the width of the intervertebral implant and parallel to the insertion path;
  wherein the first part has a midline on the outer surface of the first part and the second part has a midline on the outer surface of the second part, where the midlines are located essentially midway between the lateral planes and parallel to the insertion path and wherein the midlines extend transverse to the width of the intervertebral implant;
  a first anchor located on the outer surface of the first part and having a height in the first direction, a length extending along the first part midline and a width in the second direction, where the first anchor has a maximum height and a mid-anchor width measured at half the maximum height where the maximum height is greater than the mid-anchor width and the first anchor has a maximum length greater than the maximum height, and wherein the first anchor extends less than the first depth, and wherein the first anchor being adapted to anchor the first part in the first vertebra; and
  a second anchor located on the outer surface of the second part and having a height in the first direction and a length extending along the second part midline, and a width in the second direction, where the second anchor has a maximum height and a mid-anchor width measured at half the maximum height where the maximum height is greater than the mid-anchor width, the second anchor being adapted to anchor the second part in the second vertebra and having a maximum length greater than the maximum height;
  wherein the first and second part midlines are the only locations on the first and second part outer surfaces where an elongated anchor extends lengthwise where the elongated anchor has a height extending in the first direction, a width extending in the second direction and a length extending in the third direction and wherein the elongated anchor has a maximum length greater than a maximum height of the elongated anchor and where the elongated anchor maximum height is greater than a maximum width of the elongated anchor, and wherein the second part spherical portion is adapted to operatively engage the first part concave portion in a position with the anchors on the first part and the second part vertically oriented to be parallel to the first direction such that the spherical portion of the inner surface of the second part that is adapted to engage the concave portion of the first part is located in a different horizontal plane than the outer surface of the second part.

8. An intervertebral implant configured and dimensioned to replace a disc removed from an intervertebral space and configured to be inserted into the intervertebral space between a first vertebra and an adjacent second vertebra, the intervertebral implant having a height in a first direction, a width in a second direction, and a depth in a third direction, the first, second, and third directions being perpendicular to each other, the width of the intervertebral implant being greater than the depth, the intervertebral implant comprising:

a first part having a substantially planar outer surface facing in the first direction and adapted to engage the first vertebra and an oppositely facing inner surface that includes a concave portion, the first part outer surface having a front edge and a back edge located opposite the front edge, the first part having a first depth in the third direction between the front and back edges;

a second part having a substantially planar outer surface facing oppositely the first part outer surface and adapted to engage the second vertebra, and an oppositely facing inner surface that has a spherical portion adapted to operatively engage the concave portion of the first part, a sidewall located between and connecting the second part outer surface and the second part inner surface, and the second part inner surface having a second portion not adapted to operatively engage the concave portion of the first part where the second portion is located between the sidewall of the second part and the spherical portion;

the first and second parts being adapted for engagement with each other;

the intervertebral implant having a leading end that leads as the intervertebral implant is inserted along an insertion path into the intervertebral space and a trailing end opposite the leading end and lateral planes extending in the first direction and passing through outermost boundaries of the width of the intervertebral implant and parallel to the insertion path;

wherein the first part has a midline on the outer surface of the first part and the second part has a midline on the outer surface of the second part, wherein the midlines are located essentially midway between the lateral planes and parallel to the insertion path and wherein the midlines extend transverse to the intervertebral implant width;

a first anchor having a height in the first direction, a length extending along the first part midline, and a width in the second direction, the first anchor being adapted to anchor the first part in the first vertebra; and a second anchor having a height in the first direction, a length extending along the second part midline, and a width in the second direction, the second anchor being adapted to anchor the second part in the second vertebra;

wherein the first and second anchors each have a maximum height greater than a mid-anchor width measured at half the maximum height of the anchor and where each of the first and second anchors have a maximum length greater than the maximum height and are adapted to enter a groove in one of the first vertebra or the second vertebra as the intervertebral implant is inserted into the intervertebral space;

wherein the first and second part midlines are the only locations on the first and second part outer surfaces where an elongated anchor extends lengthwise where the elongated anchor has a height extending in the first direction, a width in the second direction and a length in the third direction and wherein the elongated anchor has a maximum length greater than a maximum height of the elongated anchor and where the maximum height is greater than a maximum width of the elongated anchor and where the elongated anchor is adapted to enter the groove in one of the first vertebra or the second vertebra as the intervertebral implant is inserted into the intervertebral space.

9. An intervertebral implant configured and dimensioned to replace a disc removed from an intervertebral space and configured to be inserted into the intervertebral space between a first vertebra and an adjacent second vertebra, the intervertebral implant having a height in a first direction, a width in a second direction, and a depth in a third direction, the first, second, and third directions being perpendicular to each other, the width of the intervertebral implant being greater than the depth, the intervertebral implant comprising:

a first part having a substantially planar outer surface facing in the first direction and adapted to engage the first vertebra and an inner surface facing oppositely the outer surface and that includes a concave portion, the first part outer surface having a front edge and a back edge located opposite the front edge, the first part having a first depth in the third direction between the front and back edges;

a second part having a substantially planar outer surface facing oppositely the first part outer surface and adapted to engage the second vertebra, and an oppositely facing inner surface that has a spherical portion adapted to operatively engage the concave portion of the first part, a sidewall located between and connecting the second part outer surface and the second part inner surface, and the second part inner surface having a second portion not adapted to operatively engage the concave portion of the first part where the second portion is located between the sidewall and the spherical portion;

the first and second parts being adapted for engagement with each other;

the intervertebral implant having a leading end that leads as the intervertebral implant is inserted along an insertion path into the intervertebral space and a trailing end opposite the leading end and lateral planes extending in the first direction and passing through outermost boundaries of the width of the intervertebral implant and parallel to the insertion path;

wherein the first part has a midline on the outer surface of the first part and the second part has a midline on the outer surface of the second part, wherein the midlines are located essentially midway between the lateral planes and parallel to the insertion path and wherein the midlines extend transverse to the width of the intervertebral implant;

a first anchor located on the outer surface of the first part and having a height extending in the first direction, a length extending along the first part midline, and a width extending in the second direction, the first anchor being adapted to anchor the first part in the first vertebra; and a second anchor located on the outer surface of the second part and having a height extending in the first direction, a length extending along the second part midline, and a width extending in the second direction, the second anchor being adapted to anchor the second part in the second vertebra;

wherein the first and second anchors each have a maximum height greater than a mid-anchor width measured at half the maximum height of the anchor and where each of the first and second anchors have a maximum length greater than the maximum height and wherein the first anchor has a first center height at a center position located at approximately a center of the midline of the first part that is greater than a height of a remainder of the first part measured between the outer surface and the inner surface of the first part at the center position; and wherein the first anchor midline is the only location on the outer surface of the first part having an anchor having a height equating to the first center height.

10. An intervertebral implant configured and dimensioned to replace a disc removed from an intervertebral space and configured to be inserted into the intervertebral space between a first vertebra and an adjacent second vertebra, the intervertebral implant having a height in a first direction, a width in a second direction, and a depth in a third direction, the first, second, and third directions being perpendicular to each other, the width of the intervertebral implant being greater than the depth of the intervertebral implant, the intervertebral implant comprising:

a first part having a substantially planar outer surface facing in the first direction and adapted for engaging the first vertebra and an oppositely facing inner surface that includes a concave portion, the first part outer surface having a front edge and a back edge located opposite the front edge, the first part having a first part depth in the third direction between the front and back edges;

a second part having a substantially planar outer surface facing oppositely the first part outer surface and adapted for engaging the second vertebra, and an inner surface facing in the first direction and consisting essentially of a substantially flat portion and a spherical portion, the second part having a sidewall located between and connecting the inner and outer surfaces, the spherical portion being adapted to operatively engage the concave portion of the first part and being located inwardly from the side wall such that the substantially flat portion surrounds the spherical portion;

the first and second parts being adapted for engagement with each other;

the intervertebral implant having a leading end that leads as the intervertebral implant is inserted along an insertion path into the intervertebral space and a trailing end opposite the leading end and lateral planes extending in the first direction and passing through outermost boundaries of the width of the intervertebral implant and parallel to the insertion path;

wherein the first part has a midline on the outer surface of the first part and the second part has a midline on the outer surface of the second part, wherein the midlines are located essentially midway between the lateral planes and parallel to the insertion path and wherein the midlines extend transverse to the width of the intervertebral implant;

a first anchor located on the outer surface of the first part and having a height extending in the first direction, a length extending along the first midline, and a width extending in the second direction, the first anchor being adapted to anchor the first part in the first vertebra, and wherein the first anchor extends less than the first part depth; and a second anchor located on the outer surface of the second part and having a height extending in the first direction, a length extending along the second part midline, and a width extending in the second direction, the second anchor being adapted to anchor the second part in the second vertebra;

wherein the first and second anchors each have a maximum height greater than a mid-anchor width measured at half the maximum height of the anchor and a maximum length greater than the maximum height and the mid-anchor width and are adapted to enter a groove in one of the first vertebra or the second vertebra as the intervertebral implant is inserted into the intervertebral space; and wherein the midlines are the only locations on the first and second part outer surfaces where an elongated anchor extends lengthwise where the elongated anchor has a height extending in the first direction, a width extending in the second direction, and a length extending in the third direction and wherein the elongated anchor has a maximum length greater than a maximum width for the elongated anchor and greater than a maximum height for the elongated anchor and adapted to enter the groove in one of the first vertebra or the second vertebra as the intervertebral implant is inserted into the intervertebral space.

* * * * *